US00PP11328P

United States Patent [19]

Plevier

[11] Patent Number: Plant 11,328

[45] Date of Patent: Apr. 4, 2000

[54] ALSTROEMERIA PLANT NAMED 'ENDLESS LOVE'

[75] Inventor: F. B. Plevier, Sassenheim, Netherlands

[73] Assignee: Koninklijke Van Zanten B.V., Hillegom, Netherlands

[21] Appl. No.: 09/106,648

[22] Filed: Jun. 29, 1998

[51] Int. Cl.[7] ..... A01H 5/00

[52] U.S. Cl. ..... Plt./309

[58] Field of Search ..... Plt./309

[56] References Cited

PUBLICATIONS

UPOV–ROM, 1999/02, Plant Variety Database, GTI Jouve Retrieval Software, citations (2) for 'Endless Love'.

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings. The varietal denomination of the new variety is 'Endless Love'.

The first act of asexual reproduction of 'Endless Love' was in Rijsenhout, The Netherlands, by propagation by tissue culture. Asexual reproduction by tissue culture in Rijsenhout, The Netherlands, has demonstrated that the combination of characteristics as herein disclosed for 'Endless Love' are firmly fixed and retained through successive generations.

SUMMARY OF THE INVENTION

The new variety of Alstroemeria, 'Endless Love', produces pink/purple blush flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Rijsenhout, The Netherlands in the month of April. Color designations indicated are in accordance with The Royal Horticultural Society Colour Chart by color plate designations.

'Endless Love' has not been observed under all possible environmental conditions. Phenotypic expression my vary with variations in environment such as temperature, light intensity, day length and growing and cultural conditions.

Botanical classification:
- *Family.*—Amaryllidaceae.
- *Genus.*—Alstroemeria sp.
- *Commercial.*—Alstroemeria hybrid.

Origin: Seedling.

Plant:
- *Form.*—Bushy, short upright growing stems.

- *Growth.*—Vigorous.
- *Height.*—About 15 to 30 cm.
- *Branching.*—No branching until umbel, stems arise from Rhizomes.
- *Flower stem.*—Length: About 15 to 30 cm. Color: Near 143C. Quantity of leaves: About 8 to 15 leaves per stem. Size of leaf: Length about 5 to 8 cm, width about 2 cm. Shape of leaf: Oblong; lanceolate shape. Texture: Top side and underside leathery. Color: Top side near 137A; underside near 137C. Venation: Linear. Stem color: Near 143C. Rhizomes: Color white; size average about 5 to 25 cm, near 155D.
- *Peduncle.*—Length: About 4 to 7 cm. Color: Near 143C. Strength: Strong. Aspect: Erect.

Bud stage:
- *Form.*—Ovoid.
- *Size.*—About 5 to 6 cm.
- *Opening.*—Buds open from the lowermost upward.
- *Color of tepals when tepals begin to unfurl.*—Near 72D.

Flower stage:
- *Time of flowering.*—Spring, summer and autumn.
- *Flower.*—Diameter: About 6 to 8 cm. Borne: Upright, at a slight angle to the perpendicular, about 2 to 5 flowers per umbel. Shape: Cup. Color: Near 53D to 56D. Discoloration after full bloom: Slight.
- *Bloom.*—Form: Tubular, open. Tepalage: About 6. Shape of tepals: Inner tepals long-obovate; outer tepals obovate shape. Margin: Medium crimped. Apex: Outer tepals slightly pointed; inner tepals pointed. Size of bloom: Diameter about 6 to 8 cm; depth about 5 to 6 cm. Texture: Smooth. Persistence: Flowers fall off after maturity. Lasting quality: About 12 to 16 days after cutting, about 3 weeks on plant.
- *Color.*—Outer tepals have a pronounced dark pink center; inner tepals strongly striped, generally white with pink center top, base light pink. Inner tepals: Near 155D with near 53D flecks, and stripes near 183A. Outer tepals: Near 56D with near 53D upper center, darker pink marking extending to tepal edge. Point of attachment: Light pink. Discoloration as bloom ages: Color is very consistent, becomes slightly more intensive as bloom matures:
- *Fragrance.*—Absent.

Reproductive organs:

*Stamens.*—About 6, near 55B. Arrangement: About side-by-side. Anthers: Near 152C. Filaments Near 55B. Pollen: Purple brown, not fertile.

*Pistils.*—1. Styles: Near 65A. Stigmas: Near 11D.

*Shape of fruit.*—Ovoid; about 1 to 1.5 cm long.

I claim:

1. A new Alstroemeria plant of the variety substantially as herein shown and described.

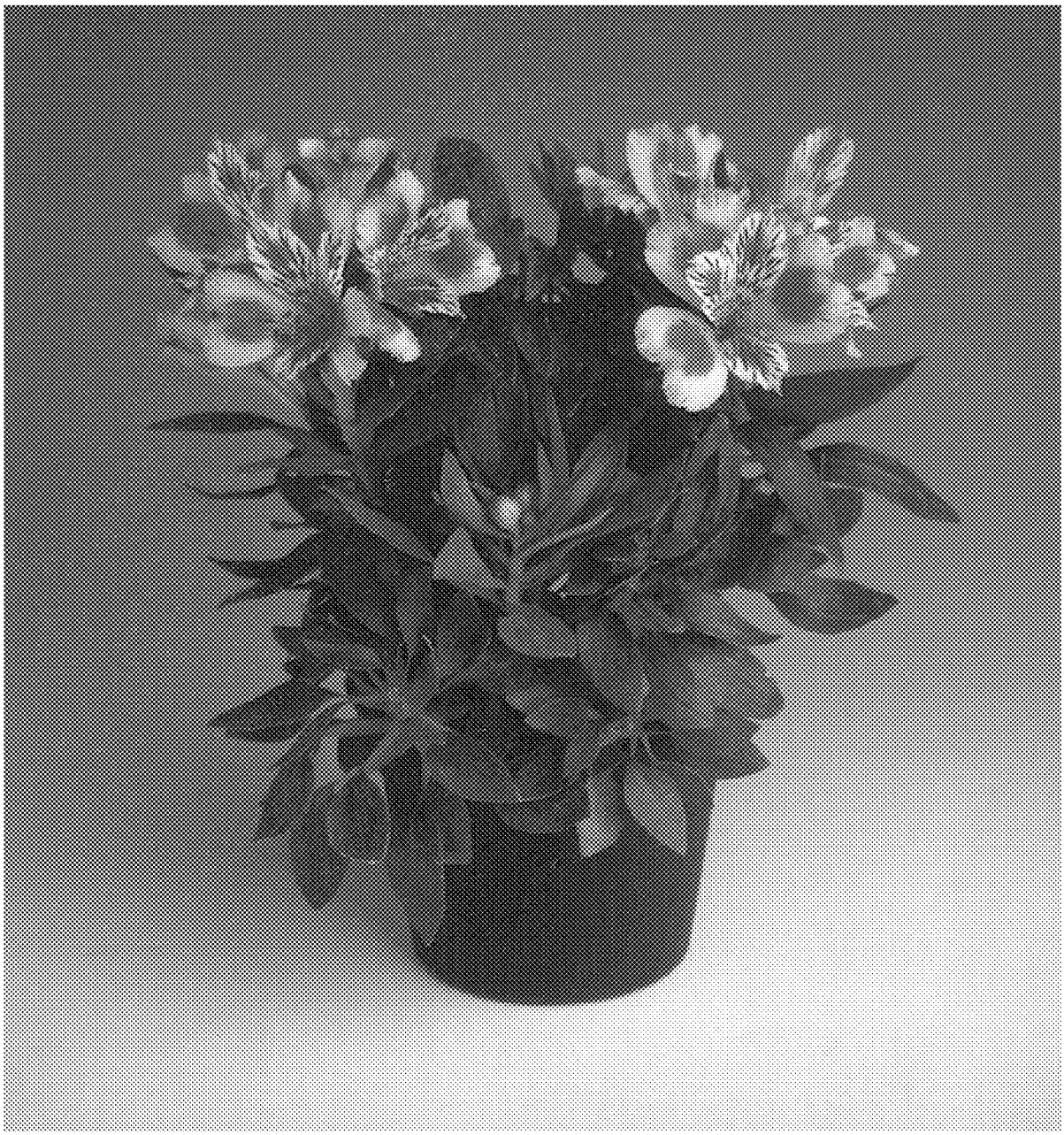

* * * * *